Figure 3:
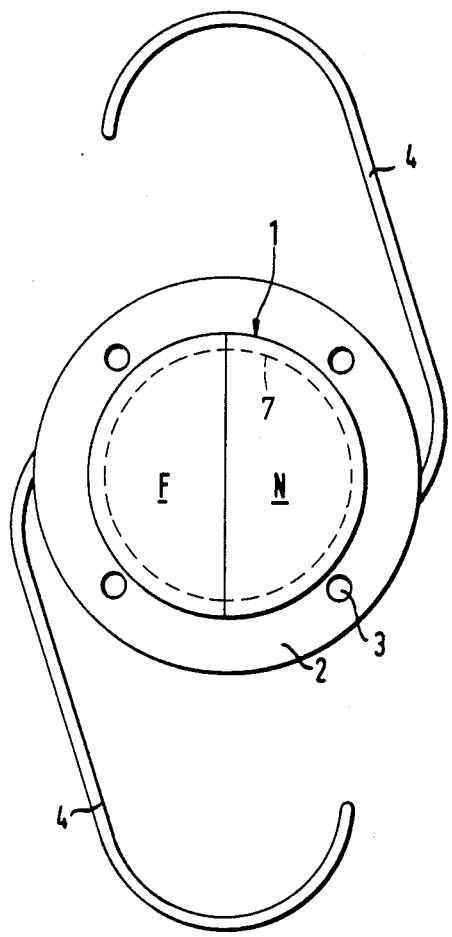

United States Patent [19]

Achatz et al.

[11] Patent Number: 4,813,955
[45] Date of Patent: Mar. 21, 1989

[54] MULTIFOCAL, ESPECIALLY BIFOCAL, INTRAOCULAR, ARTIFICIAL OPHTHALMIC LENS

[76] Inventors: Manfred Achatz, Feldstrasse 11, 6477 Limeshain 2; Peter Höfer, Karlsbader Strasse 50, 8750 Aschaffenburg; Jürgen Strobel, Zeppelinstrasse 14a, 3550 Marburg, all of Fed. Rep. of Germany

[21] Appl. No.: 648,639

[22] Filed: Sep. 7, 1984

[30] Foreign Application Priority Data

Sep. 7, 1983 [DE] Fed. Rep. of Germany ....... 3332313

[51] Int. Cl.[4] ............................ A61F 1/16; A61F 1/24
[52] U.S. Cl. ...................................................... 623/6
[58] Field of Search ............................................. 623/6

[56] References Cited

U.S. PATENT DOCUMENTS 4,010,496  3/1977  Neefe ...................................... 623/6
4,618,228  10/1986  Baron et al. ........................... 623/6

Primary Examiner—V. Millin
Attorney, Agent, or Firm—Felfe & Lynch

[57] ABSTRACT

A multifocal, especially bifocal, intraocular, artificial ophthalmic lens of transparent material, whose optical lens portion is divided into near range and far range zones and, each of which is disposed on the optical lens portion with approximately equal surface proportions and symmetrically with the lens axis.

17 Claims, 3 Drawing Sheets

FIG.1
FIG.2
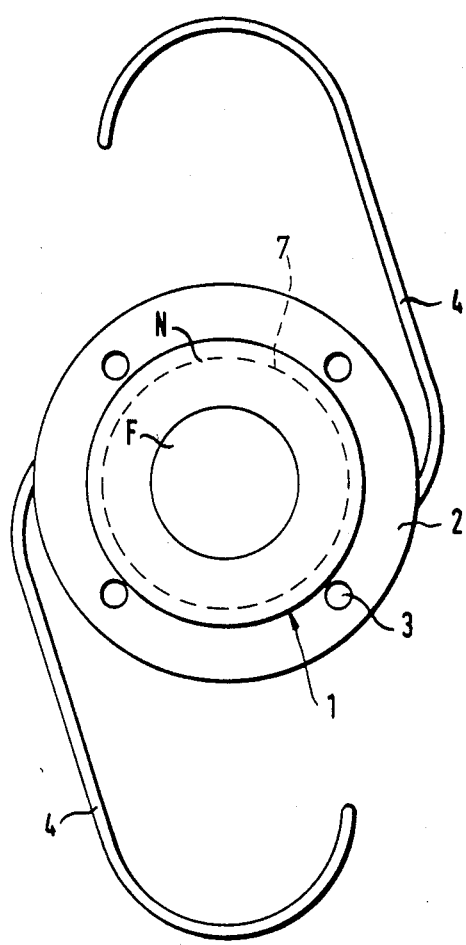
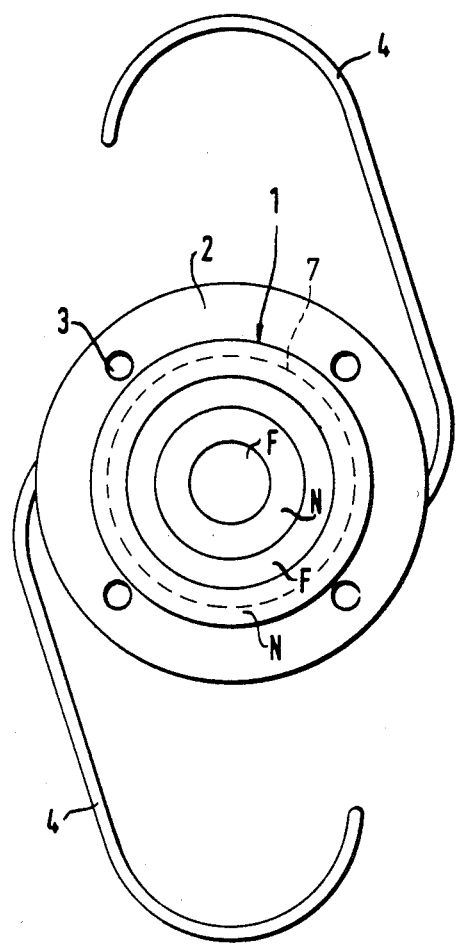

MULTIFOCAL, ESPECIALLY BIFOCAL, INTRAOCULAR, ARTIFICIAL OPHTHALMIC LENS

The invention relates to a multifocal, especially bifocal, intraocular, artificial opthalmic lens having an optical lens portion of transparent material which covers the pupil of the iris.

An artificial bifocal opthalmic lens based on the alternating or shifting segment principle, in which either only the near range or only the far range of the vision aid is in the ray path and thus is active, is disclosed in U.S. Pat. No. 4,010,496. This lens is provided in the bottom lens portion with a segment-shaped near-focus part. The segment-shaped near focus part and the segment-shaped far focus part situated above it meet at a line of separation. It is a disadvantage of this type of lens that a discontinuity in the image occurs at the line of separation. Furthermore, it has been found that, if at least three quarters of the pupil area is not covered by one or the other zone of sharp focus, double vision and contrast losses develop. It is therefore extremely difficult to determine the correct segment height or the correct shape of the line of separation.

It is the object of the invention, therefore, to create an artificial ophthalmic lens of the kind described above, whereby images of objects at different distances from the observer will be produced simultaneously on the retina, so that the sharp image can be utilized and the blurred image suppressed.

This object is achieved by the invention by disposing near range and far range zones on a transparent optical lens portion of an artificial, intraocular, ophthalmic lens with approximately equal areas symmetrically from the axis of the optical lens portion.

An intraocular lens based on the simultaneous principle is thereby created in which sharp vision is possible simultaneously in the near and far ranges after implantation, because both the lens portions for near vision and the lens portions for far vision are simultaneously in the ray path of the optical lens portion of the ophthalmic lens.

In an advantageous manner, the pupil diameter can be set either during the implantation operation or later by medicinal or microsurgical measures to the optical lens portion to bring the optical lens portion perfectly into the ray path.

The artificial intraocular ophthalmic lens can be designed variously, e.g., as a vitreous-chamber-fixed, anterior-chamber-fixed or iris-fixed lens.

Examples of the embodiment of the intraocular lens according to the simultaneous principle are obtained by the concentric arrangement of the near and far portions, by vertical division of the lens area into a near-effect zone and a far-effect zone, and by dividing the lens area into radially extending areas of near and far effect.

In the embodiment in which the optically active area of the intraocular lens is divided into the near and far range zones in a plurality of concentric annular areas which are disposed alternately in the radial direction, it is also accomplished that visual capacity is not impaired by rapid shifts from bright to dark. This effect can be further enhanced if the ratio of the area of an annular near focus portion to the area of the adjacent annular far focus portion is kept sufficiently constant from the lens center radially toward the lens margin. If the pupil opens rapidly upon a rapid change from light to dark, the area ratio of the near and far range zones remains equal, thus preventing reduction of vision and impairments in seeing.

If the far focus portion is disposed in the center of the optical lens portion, and the near focus portion outside, the optical action of the concentric annular areas which form the near focus part and the far focus part can run progressively radially outwardly. This means that the refractive power increases from the center to the periphery, and this increase in the vertex index of refraction takes place preferably continuously radially from the center to the periphery. If, vice versa, the near focus portion is arranged in the center of the optical lens portion and the far focus portion at the periphery, the optical action of the concentric annular areas which form the near focus portion and the far focus portion can run progressively radially towards the center. This means, then, that the refractive power decreases from the center towards the periphery, this decrease in the refractive power preferably taking place continuously.

It is also possible to divide the near range and far range zones into several sectors of equal angles and to dispose them alternately around the optical axis.

It is furthermore possible to provide the near and far range zones each in one half of the optical lens portion, with the transition or line of separation between the near range zone and the far range zone in the lens implanted in the eye running from the top margin of the lens to the opposite bottom margin of the lens, and the near range zone in the nasal portion of the lens (closer to the wearer's nose) and the far range zone in the temporal lens portion (farther from the wearer's nose). In this case again, brightness differences have no effect, and the lens is independent of pupillary action. Even in the case of pupil dilation occurring due to low lighting and at night, this does not lead to greater blurring of vision, because the percentages (area ratio) by which the far focus portion and the near focus portion are simultaneously covered remain equal.

In the lenses of the invention, images of far objects and near objects are projected simultaneously on the retina. In the central nervous system, the image on which the wearer of the artificial intraocular eye lens is concentrating is selected. An image discontinuity as in the case of the known alternating bifocal ophthalmic lens does not occur. The near and far range zones can be formed on the front and/or back of the optical lens portion. The optical effects of the near and far range zones can be achieved by appropriate surface working of the lens body or by combining materials of different index of refraction. For the achievement of a stenopeic effect, i.e., a greater depth of focus, as in the pinhole camera effect, the lens material can be masked off or darkened peripherally such that a pinhole remains in the center, with a diameter, for example, of the order of 0.5 to 2 mm. An object is projected by this pinhole by means of a narrow bundle of rays. This makes the scatter circles on the retina of the anetrobe eye smaller and thus improves image sharpness.

Another advantageous development consists in the fact that at least the optical lens portion is formed of a flexible, transparent envelope filled with a transparent fluid, which can be attached to the ciliar muscles. When the ciliary muscle contracts, the lens which is at first under tension and therefore more flattened becomes more spherical and thus is given a greater refractive power. To this degree, a continuous changeover of focus between near vision and far vision can be made possible by the deformation of the lens fashioned in this manner.

Figure 4:
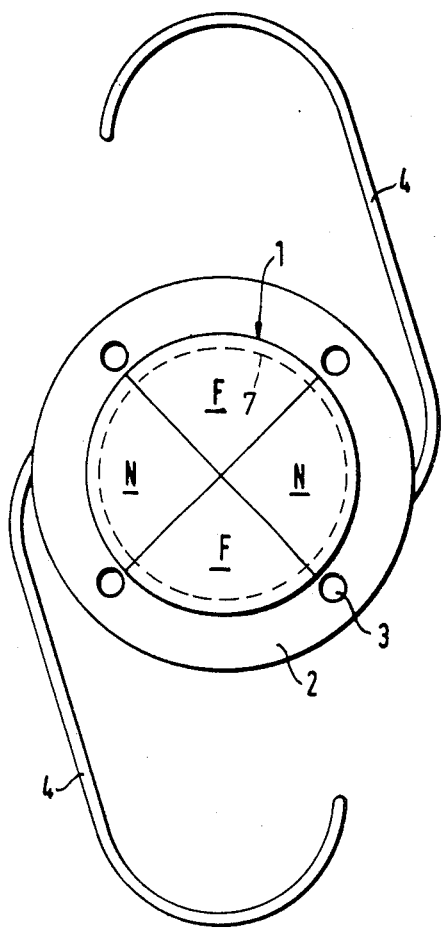
Figure 5:
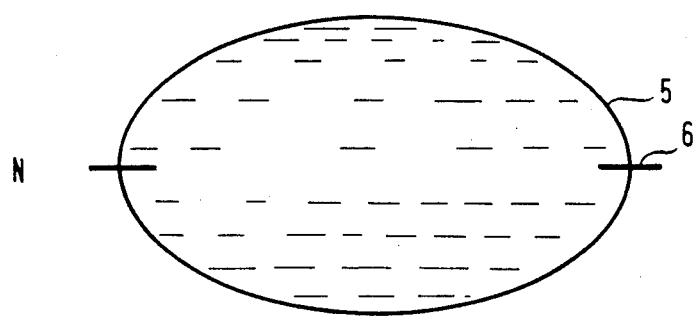
Figure 6:
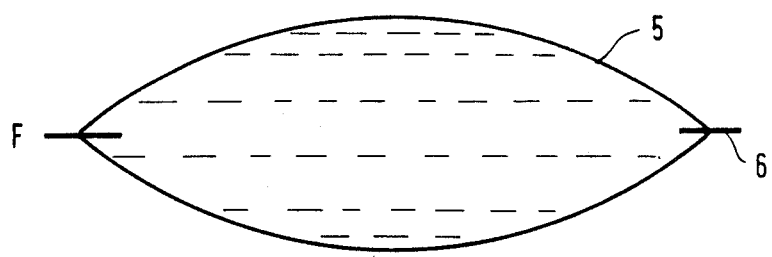
Figure 7:
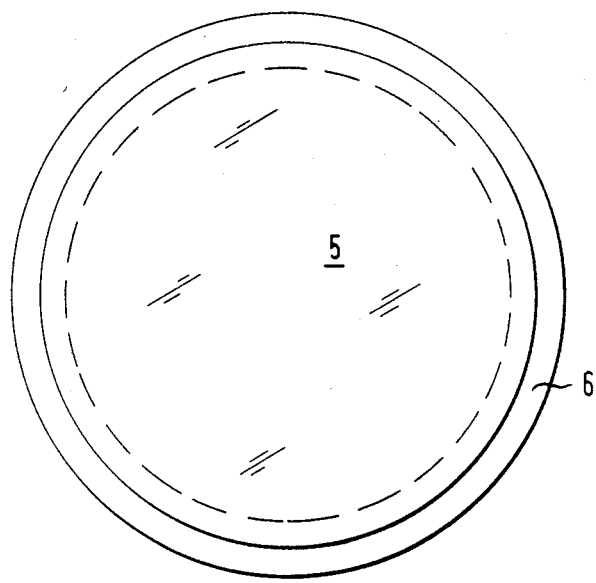

The invention is further explained by embodiments with the aid of the appended drawings, wherein:

FIG. 1 shows a first embodiment of a bivisual artificial intraocular lens in which a near range zone and a far range zone are disposed concentrically with one another, FIG. 2 shows an embodiment of an artificial, intraocular ophthalmic lens in which near range zones and far range zones are formed by concentric annular surfaces, FIG. 3 shows an embodiment in which the optical lens portion is divided into two halves by a vertical line separating it into a near range zone and a far range zone, FIG. 4 shows an embodiment having sector-shaped near and far range zones, FIG. 5 shows an embodiment of the intraocular lens which is formed by an envelope filled with a transparent fluid, in the state for near vision, FIG. 6 shows the embodiment represented in FIG. 5, in the state for far vision, FIG. 7 is a top view of the embodiment represented in FIGS. 5 and 6.

In the embodiment of a bivisual intraocular lens of FIG. 1, an optical lens portion 1 has a far range zone F disposed in the center in the form of a circular area, and concentrically around it, a near range zone N in the form of an annular area. However, the far range portion F can also be disposed in the center and the near portion N around it. The lens body has bores 3 as near as possible to the circumferential margin of the lens, in a peripheral annular lens portion 2 surrounding the optical lens portion 1, so to avoid interference with the optical function of the lens. Holding loops 4 serve to fix the lens in the eye. The normal size and position of the pupil is indicated by the dashed line 7.

The embodiment shown in FIG. 2, of a multifocal, intraocular artificial ophthalmic lens has in the center of the optical lens portion 1 a far range zone F in the form of a circular area, and an annular near range zone N disposed concentrically around it; these are followed radially towards the periphery by additional annular, concentrically-disposed, far and near range zones F and N. It is also possible, however, to dispose the near range zone N in the center of the optical lens portion 1 and a concentric annular far range zone F around it, and so on. In the peripheral annular lens portion 2, which is not optically active, the bores 3 are provided, whereby, as in the embodiment in FIG. 1, the lens can be turned to a suitable position, if necessary, after the implantation of the lens and before the final closing of the eye. These bores 3 are so arranged that they do not interfere with the optical functioning of the lens. The lens furthermore has the holding loops 4 whereby the lens can be fixed.

The embodiment in FIG. 3 is of the bivisual type like the embodiment in FIG. 1, but the line of separation between the near range zone N and the far range zone F runs, when the lens body is installed, from the upper margin of the lens to the bottom margin of the lens, and separates the optical lens portion 1 into two halves of which the one half forms the far range zone F and the other half the near range zone N. With the lens inserted into the eye, the near range zone N is situated closer to the wearer's nose than the far range zone F. In this example, again, the bores 3 are disposed in a lens area close to the lens margin, so that the optical function of the lens will not be impaired. Holding loops 4 serve to fix the lens in the eye.

In the embodiment represented in FIG. 4, two far range zones F and two near range zones N of sector shape are provided, and have equal sector angles. In the embodiment represented, the sector angles are 90°. It is, however, also possible to provide a greater number of near and far range zones with correspondingly smaller sector angles. The near and far range zones N and F are disposed alternately around the lens axis. Bores 3 are situated in a peripheral lens portion 2, which is optically inactive. Fixation means 4 again serve to fix the lens in the eye.

Other fixation means can be provided for the artificial opthalmic lens. Known fixation means are described in German patent publication Nos. 25 04 540, 26 05 847, 26 54 999 and 27 25 219.

As may be seen in the embodiments of FIGS. 1-4 the near and far range zones (N and F) of the transparent optical lens portion immediately in front of the pupil have approximately equal areas symmetrically from the axis of the optical lens.

In FIG. 5, there is shown in section an embodiment of an artificial intraocular lens which consists of a flexible, transparent envelope 5 filled with a transparent fluid. This envelope 5 with the fluid therein substantially forms the optical lens portion. In FIG. 5 is represented the state of the lens for near vision. The envelope filled with the transparent fluid is attached to the ciliary muscle of the eye by means of a fastening fringe 6 which is anchored in the envelope. In this manner the ciliary muscle acts as it does on the natural eye lens, i.e., when the ciliary muscle contracts, the illustrated near action of the lens respresented in FIG. 5 results, since the lens becomes more spherical and thus receives a greater refracting power. When the ciliary muscle elongates, a tension is exerted on the envelope 5 filled with the transparent fluid and flattens the latter so that it is given the shape represented in FIG. 6. The lens then has a reduced refracting power, and serves for far vision. In this manner a continuous change of focus from near vision to far vision can be made possible in conjunction with the action of the ciliary muscle.

In FIG. 7 is shown a top view of the embodiment represented in cross section in FIGS. 5 and 6, and the anchoring of the fastening fringe 6 in the flexible envelope body 5 can also be seen.

It will be understood that the specification and examples are illustrative but not limitative of the present invention and that other embodiments within the spirit and scope of the invention will suggest themselves to those skilled in the art.

What is claimed is:

1. In a multifocal, especially bifocal, artificial, intraocular, ophthalmic lens adapted to be implanted in the eye at a fixed position and having a transparent optical lens portion for covering the pupil of the iris and means for holding said lens portion in a fixed position in the eye, the improvement wherein near range and far range zones (N and F) of the optical lens portion have approximately equal areas symmetrically about the axis of the optical lens portion, such that rays received by the pupil of the eye in which the lens is fixed pass through both near and far range zones of the lens of approximately equal area, for simultaneous, sharp near and far vision.

2. Ophthalmic lens of claim 1, characterized in that the near range and far range zones (N and F) are concentric with one another.

3. Ophthalmic lens of claim 1, characterized in that the near range and far range zones (N and F) comprises radially-alternating, concentric annular areas.

4. Ophthalmic lens of claim 1, characterized in that the area ratio (area or areas of the near range zone: area or areas of the far range zone) is at least effectively constant radially from the axis of the optical lens portion.

5. Ophthalmic lens of claim 2, characterized in that the far range zone (F) is in the center of the optical lens portion (1).

6. Ophthalmic lens of claim 3, characterized in that the far range zone is in the center of the optical lens portion and the refractive power of the concentric annular areas changes progressively radially from the axis of the optical lens portion.

7. Ophthalmic lens of claim 2, characterized in that the near range zone (N) is in the center and the far portion (F) around it.

8. Ophthalmic lens of claim 3, characterized in that the near range zone is in the center of the optical lens portion and the refractive power of the concentric annular areas changes progressively radially towards the axis of the optical lens portion.

9. Ophthalmic lens of claim 1, characterized in that the near and far range zones (N and F) are alternate, radially-extending sectors of equal angles around the axis of the optical lens portion.

10. Ophthalmic lens of claim 1, characterized in that the transition between the near and far range zones (N and F) runs from one margin to the opposite margin of the optical lens portion (1), that means orienting the lens when implanted in the eye orients the transition between the near and far range zones from the upper to the lower lens margin for dividing the optical lens portion (1) into a nasal (lying near the wearer's nose) and a temporal (lying remote from the wearer's nose) zone with the near range zone (N) lying nasally and the far range zone (F) lying temporally.

11. Ophthalmic lens of claim 1, characterized in that the near and far range zones (N and F) are formed on at least one of the front and rear faces of the optical lens portion (1).

12. Ophthalmic lens of claim 11, characterized in that at least one of the far and near zones is biconvexly curved on both of the faces of the optical lens portion.

13. Ophthalmic lens of claim 1, characterized in that the near and far range zones (N and F) are formed by materials of different index of refraction.

14. Ophthalmic lens of claim 1, characterized in that the near and far range zones (N and F) are formed by a material having a refractive index gradient in the radial direction from or towards the axis of the optical lens portion.

15. Ophthalmic lens of claim 1, characterized in that the near and far range zones (N and F) are a shaped surface of the optical lens portion (1).

16. Ophthalmic lens of claim 1, characterized in that the optical lens portion (1) is so limited around its axis that depth of focus of the image therefrom (stenopeic effect) is achieved.

17. Ophthalmic lens of claim 16, characterized in that the limitation around the axis of the optical lens portion is a pinhole surrounded by at least partially opaque lens material.

* * * * *